United States Patent
Haase et al.

(10) Patent No.: US 7,999,128 B2
(45) Date of Patent: Aug. 16, 2011

(54) HYDROXYBENZOPHENONE DERIVATIVES

(75) Inventors: Jürg Haase, Bettingen (CH); Stefan Müller, Weil am Rhein (DE); Thomas Ehlis, Freiburg (DE)

(73) Assignee: BASF SE, Ludwigshafen (DE)

( * ) Notice: Subject to any disclaimer, the term of this patent is extended or adjusted under 35 U.S.C. 154(b) by 238 days.

(21) Appl. No.: 12/223,686

(22) PCT Filed: Feb. 6, 2007

(86) PCT No.: PCT/EP2007/051117
§ 371 (c)(1),
(2), (4) Date: Nov. 20, 2008

(87) PCT Pub. No.: WO2007/090832
PCT Pub. Date: Aug. 16, 2007

(65) Prior Publication Data
US 2009/0220439 A1 Sep. 3, 2009

(30) Foreign Application Priority Data
Feb. 9, 2006 (EP) .................... 06101454

(51) Int. Cl.
*C07F 7/04* (2006.01)
(52) U.S. Cl. ........ 556/467; 556/400; 556/465; 556/466
(58) Field of Classification Search ........................ None
See application file for complete search history.

(56) References Cited

U.S. PATENT DOCUMENTS

| | | | |
|---|---|---|---|
| 2,938,047 A | 5/1960 | Black | 60/448.2 |
| 4,042,613 A | 8/1977 | Takamizawa et al. | 260/448.2 |
| 4,495,360 A | 1/1985 | Anthony | 556/436 |
| 5,270,426 A * | 12/1993 | Sakuta et al. | 528/15 |
| 5,756,793 A | 5/1998 | Valet et al. | 556/436 |
| 6,071,052 A | 6/2000 | Kerr | 424/59 |
| 6,409,995 B1 * | 6/2002 | Habeck et al. | 424/59 |
| 7,388,102 B2 * | 6/2008 | Berg-Schultz et al. | 556/436 |
| 2002/0001570 A1 | 1/2002 | Heidenfelder et al. | 424/59 |
| 2003/0152598 A1 | 8/2003 | Heidenfelder et al. | 424/401 |
| 2005/0008587 A1 | 1/2005 | Schulz et al. | 424/59 |
| 2005/0255066 A1 | 11/2005 | Berg-Schultz et al. | 424/70.1 |
| 2006/0018846 A1 | 1/2006 | Haase et al. | 424/59 |

FOREIGN PATENT DOCUMENTS

| | | |
|---|---|---|
| DE | 10011317 | 9/2001 |
| WO | 93/10745 | 6/1993 |
| WO | 2006/128614 | 12/2006 |

OTHER PUBLICATIONS

English Language Abstract of DE 10011317, Sep., 13, 2001.
English language abstract of JP 03287588, Dec. 18, 1991.

* cited by examiner

*Primary Examiner* — Sudhakar Katakam
(74) *Attorney, Agent, or Firm* — Shiela A. Loggins

(57) ABSTRACT

Disclosed are hydroxyphenylbenzophenone derivatives of formula (1), wherein $R_1$ and $R_2$ independently from each other are hydrogen; $C_1$-$C_{20}$alkenyl; $C_3$-$C_{10}$cycloalkyl; or $R_1$ and $R_2$ together with the linking nitrogen atom form a 5-6-membered heterocyclic ring; $R_3$, $R_4$ and $R_5$ independently from each other are $C_1$-$C_4$alkyl; $C_1$-$C_4$alkoxy; or a radical of formula (1a) $R_6$ is $C_1$-$C_6$alkyl; and A is a straight-chain or branched $C_3$-$C_6$alkylene, which is optionally interrupted by one or more *—O—*, or *—O—(CO)—* groups; and m is 0; or a number from 1 to 5. The compounds are useful as cosmetic UV filters with outstanding solubility properties in cosmetic oils.

(1)

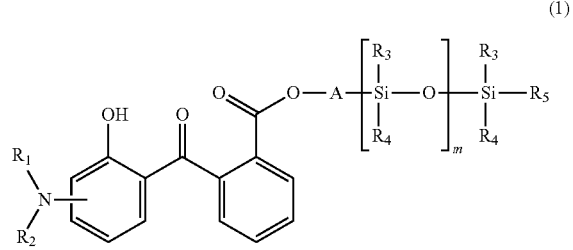

8 Claims, No Drawings

HYDROXYBENZOPHENONE DERIVATIVES

The present invention relates to hydroxybenzophenone UV absorbers, to the preparation of these compounds, to the use of these compounds for protecting human and animal skin and hair from the harmful effects of UV radiation, and to their use in cosmetic and pharmaceutical formulations.

It is known that certain organic UV filters, such as, for example, poorly soluble benzophenone derivatives, have pronounced UV filter properties. However, the solubility of such organic UV filters in solvents like Cyclomethicone (cyclopentasiloxane) that are suitable for specific cosmetic formulations like sprays wherein the active is dissolved in Cyclomethicone and silicon oils is often inadequate.

There is a strong interest in organic light-protective filters that can be readily incorporated in cosmetic formulations that is to say that have good oil-solubility.

The problem of the present invention is therefore to find organic UV filters or mixtures of UV filters that have good solubility in solvents that are suitable for cosmetic formulations.

It has now been surprisingly found that UV absorber compositions comprising selected silylated benzophenone derivatives have such properties.

The present invention therefore refers to hydroxyphenyl-benzophenone derivatives of formula,

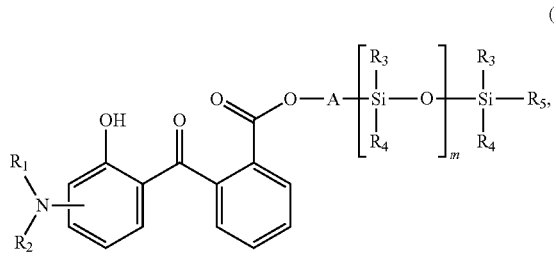

(1)

wherein
$R_1$ and $R_2$ independently from each other are hydrogen; $C_1$-$C_{20}$alkyl; $C_2$-$C_{20}$alkenyl; $C_3$-$C_{20}$cycloalkyl; $C_3$-$C_{10}$cycloalkenyl; or $R_1$ and $R_2$ together with the linking nitrogen atom form a 5- 6-membered heterocyclic ring;
$R_3$, $R_4$ and $R_5$ independently from each other are $C_1$-$C_4$alkyl; $C_1$-$C_4$alkoxy or a radical of formula

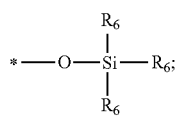

(1a)

$R_6$ is $C_1$-$C_4$alkyl;
A is a straight-chain or branched $C_3$-$C_6$alkylene, which is optionally interrupted by one or more *—O—*, or *—O—(CO)—* groups; and
m is 0; or a number from 1 to 5.

$C_1$-$C_{20}$alkyl denotes a linear or branched, unsubstituted or substituted alkyl group such as, for example, methyl, ethyl, propyl, isopropyl, n-butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-(2,4-di-tert-amylphenoxy)-propyl, ethoxycarbonylmethyl-2-(2-hydroxyethoxy)ethyl or 2-furylethyl.

$C_2$-$C_{20}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_3$-$C_{10}$cycloalkyl is for example cyclopropyl, cyclobutyl, cyclopentyl, cycloheptyl, cyclooctyl, cyclononyl or cyclodecyl and preferably cyclohexyl. These radicals may be substituted, for example by one or more or equal or different $C_1$-$C_4$alkyl radicals, preferably by methyl, and/or hydroxy. If cycloalkyl radicals are substituted by one or more radicals, they are preferably substituted by one, two or four, preferably by one or two equal or radicals.

$C_3$-$C_{10}$cycloalkenyl is for example cyclopropenyl, cyclobutenyl, cyclopentenyl, cycloheptenyl, cyclooctenyl, cyclononenyl or cyclodecenyl and preferably cyclohexenyl. These radicals may be substituted with one or more equal or different $C_1$-$C_4$alkyl radical, preferably with methyl, and/or hydroxy. If cycloalkenyl radicals are substituted with one or more radicals they are preferably substituted with one, two, three or four, preferably with one or two equal or different radicals.

Hydroxy substituted $C_1$-$C_5$alkyl groups are for example hydroxymethyl, hydroxyethyl, hydroxypropyl, hydroxybutyl or hydroxypentyl.

$C_1$-$C_6$alkylene is for example methylene, ethylene, propylene, butylenes or hexylene.

The alklyene radicals may optionally be substituted by one or more $C_1$-$C_5$alkyl radicals.

If $R_1$ and $R_2$ are heterocyclic radicals, these comprise one, two, three or four equal or different ring hetero atoms. Special preference is given to heterocycles which contain one, two or three, especially one or two, identical or different hetero atoms. The heterocycles may be mono- or poly-cyclic, for example mono-, bi- or tri-cyclic. They are preferably mono- or bi-cyclic, especially monocyclic. The rings preferably contain 5, 6 or 7 ring members. Examples of monocyclic and bicyclic heterocyclic systems from which radicals occurring in the compounds of formula (1) may be derived are, for example, pyrrole, furan, thiophene, imidazole, pyrazole, 1,2,3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothiophene, benzofuran, pyrrolidine, piperidine, piperazine, morpholine and thiomorpholine.

In the compounds of formula (1) $R_1$ and $R_2$ are preferably $C_1$-$C_{20}$alkyl, more preferably $C_1$-$C_5$alkyl and most preferably $R_1$ and $R_2$ in formula (1) have the same definition In the compounds of formula (1) A is preferably $C_3$-$C_6$alkylene; or ($C_1$-$C_5$alkylene)-O—(CO)—($C_1$-$C_5$)alkylene.

In formula (1) m is preferably 0.

$R_3$ and $R_4$ in formula (1) are preferably a radical of formula

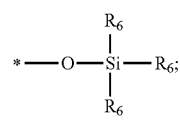

(1a)

wherein
$R_6$ is $C_1$-$C_6$alkyl.
Most preferred are compounds of formula (1), wherein $R_1$ and $R_2$ are $C_1$-$C_5$alkyl;

$R_3$ and $R_4$ are a radical of formula

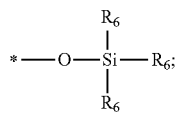

$R_6$ is $C_1$-$C_5$alkyl;
A is $C_3$alkylene; and
m is 0.

The compounds of formula (1) may be prepared by a manner known per se.

Usully they are prepared by reacting a siloxanol compound of formula

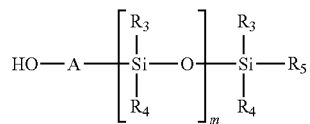

with a benzophenone carboxylic acid or anhydride of the formula

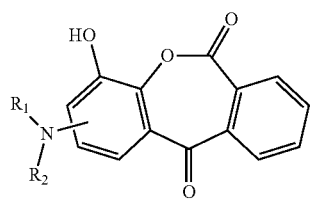

according to the following reaction scheme:

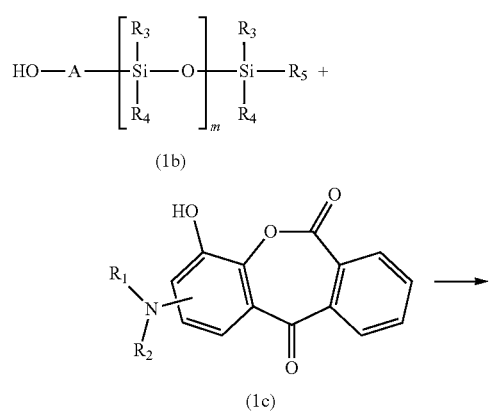

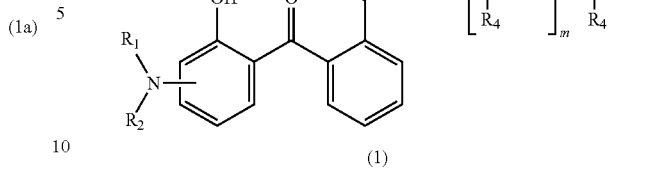

$R_1$ and $R_2$, $R_3$, $R_4$ and $R_5$, A and m are defined as in formula (1).

Another preparation route comprises hydrosilylation of the unsaturated ester of benzophenone carboxylic acid e.g. Allylesters using known Catalyst (Pt, Cu) and corresponding hydrosiloxane.

The reaction is usually carried out at a temperature from 25 to 200° C. Generally a solvent is not necessary for this reaction. If a solvent is used however, preferably the solvents as used in the working examples are preferred.

The reaction time is usually from 0.5 to 20 h.

The starting compounds of formula

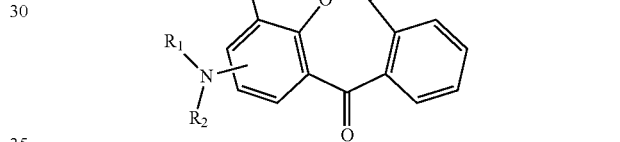

are known from the prior art, for example WO 2004/052837.

They are prepared by a manner known per se by dehydratisation of the compound of formula

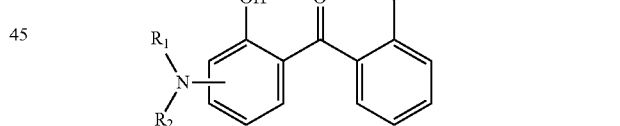

to the compound of formula (1c)

$R_1$ and $R_2$ are defined as in formula (1).

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds are preferably used in dissolved form.

The cosmetic formulations or pharmaceutical compositions according to the present invention may additionally contain one or more than one further conventional UV filter.

The cosmetic or pharmaceutical preparations may be, for example, creams, gels, lotions, alcoholic and aqueous/alcoholic solutions, emulsions, wax/fat compositions, stick preparations, powders or ointments. In addition to the above-mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, esters of fatty acids, natural or synthetic triglycerides including glyceryl esters and derivatives, pearlescent waxes, hydrocarbon oils, silicones or siloxanes, organosubstituted super-fatting agents, surfactant consistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, polymeric beads or hollow spheres as spf enhancers.

Cosmetic or Pharmaceutical Preparations

Cosmetic or pharmaceutical formulations are ingredients in a wide variety of cosmetic preparations. The following preparations are of special interest:

skin-care preparations, e.g. skin-washing and cleansing preparations in the form of tablet-form or liquid soaps, soapless detergents or washing pastes; or skin emulsions, multi-emulsions or skin oils;

bath preparations, e.g. liquid (foam baths, milks, shower preparations) or solid bath preparations, e.g. bath cubes and bath salts;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hairfoams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic preparation according to the invention is distinguished by excellent protection of human skin against the damaging effect of sunlight.

EXAMPLES

A. Preparation Examples

Example A1

Preparation of the Compound of Formula

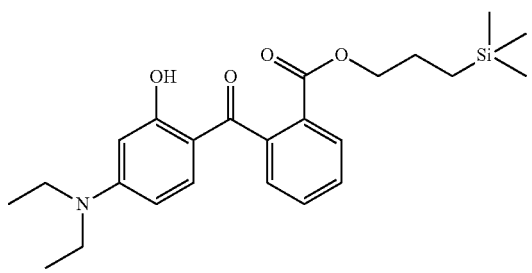
(101)

6.8 g 3-(trimethylsilyl)-1-propanol,
0.1 g 4-dimethylaminopyridine and
14.8 g diethylamino-dibenzo-oxepine-6,11-dione corresponding to formula

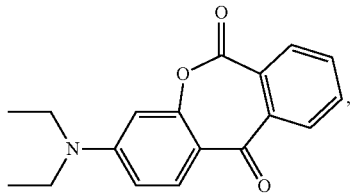
(101a)

dissolved in 70 ml toluene are stirred during 7 h at 75-85° C. in an oil bath.

The reaction mass is worked off after evaporation with column chromatography (silicagel 60/toluene: acedic acid ethyl ester).

8 g of a pure product (bright-yellow oil) is obtained.

Eemental analysis: C=67.2%, H=7.9%, N=3.2% (Th: C=67.4%, H=7.8%, N=3.3%) $\lambda_{max}$=350 nm; E 1/1=822.

The obtained compound is soluble in Cyclomethicone (solubility in Cyclomethicone is 1.8% at RT).

Example A2

Preparation of the Compound of Formula

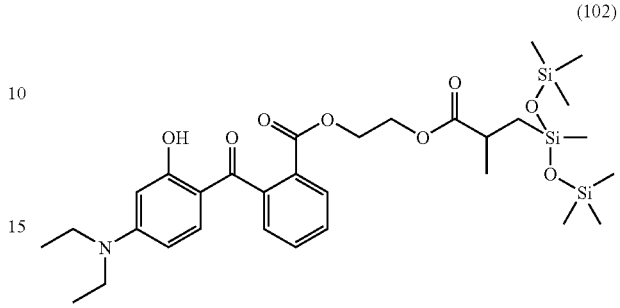
(102)

4.0 g 1,1,1,3,5,5,5-heptamethyl-trimethyl-silyl-propanol, prepared by hydrosilylation of allylalcohol with 1,1,1,3,5,5,5-heptamethyl-trimethylsiloxane,
14.8 g diethylamino-dibenzo-oxepine-6,11-dione and
0.1 g 4-dimethylaminopyridine
are reacted in toluene as described in Example 1 and worked off.

About 8 g of a pure endproduct of a yellow viscous oil (by determination via column chromatography) are obtained.

Elemental analysis: C, H, N in accordance with the theory.
$\lambda_{max}$=350 nm; E 1/1=571

The solubility in Cyclomethicone at RT is >20%.

Example A3

Preparation of the Compound of Formula

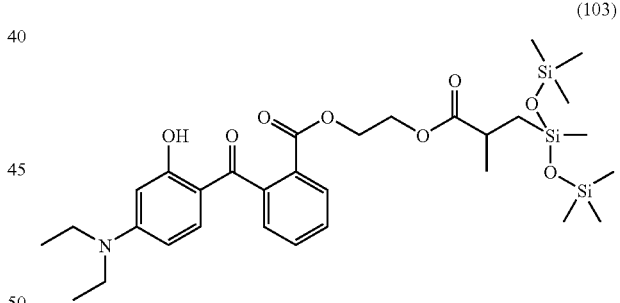
(103)

26 g of the compound of formula and 58.8 g of the compound of formula (101a) are mixed together with 200 ml propyl acetate.

0.4 g 4-(dimethylamino)-pyridine and 1 g hydrochinone monomethylether are added and heated up to 95° C. within 3 h.

The mixture is concentrated to a volume of about 100 ml with the rotating evaporator and 600 ml methanol are added.

Colorless crystals of the compound of formula

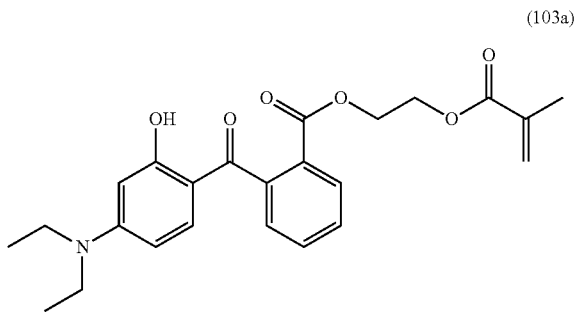

(103a)

are formed overnight.

12.8 g of the compound of formula (103a) are added to 50 ml 1-butanol and heated up to about 80° C. (under inert gas).

9.0 g of the compound of formula

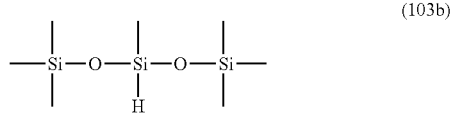

(103b)

and 5 drops of a Karstedt-catalysator (Aldrich) are dissolved in 10 ml 1-butanol and added dropwise within 30 min.

The solution is stirred at 80° C. for 8 h.

After concentration the raw product is purified via column chromatography to obtain the compound of formula (103).

$\lambda_{max}$=357 nm; E 1/1=606

B. Application Examples

Examples B1-B6

Six formulations of water silicone type are prepared. All formulation show high efficacy and an outstandingly smooth skin feel.

Examples B1 to B3 are water silicone formulations wherein the compound of formula (102) is used as silicone soluble UV-A filter.

Examples B4 to B6 are water silicone formulations wherein the compound of formula (103) is used as silicone soluble UV-A filter.

High SPF values and high UVA protection are obtained as shown in Table B1.

TABLE B1

| | | water silicone formulations | | | | | |
|---|---|---|---|---|---|---|---|
| | INCI-Name/ | % w/w (as supplied) | | | | | |
| | Chemical-Name | Ex. B1 | Ex. B2 | Ex. B3 | Ex. B4 | Ex. B5 | Ex. B6 |
| Part A | Cetyl PEG/PPG-10/1 Dimethicone | | | | | | |
| | Isononyl Isononanoate | 2.80 | 2.80 | 2.80 | 2.80 | 2.80 | 2.80 |
| | Cetyl Dimethicone | 4.00 | 4.00 | 4.00 | 4.00 | 4.00 | 4.00 |
| | Silica Dimethyl Silylate | 1.00 | 1.00 | 1.00 | 1.00 | 1.00 | 1.00 |
| | Ethylhexyl Methoxy-cinnamate | 0.30 | 0.30 | 0.30 | 0.30 | 0.30 | 0.30 |
| | Octocrylene | 6.00 | 6.00 | 8.00 | 6.00 | 6.00 | 8.00 |
| | Compound of formula (102) prepared according to Example A2 | 3.00 | 3.00 | 300 | | | |
| | Compound of formula (103) prepared according to Example A3 | | | | 3.00 | 3.50 | 3.50 |
| | Bis-Ethylhexyloxyphenol Methoxyphenyl Triazine | 3.00 | 3.50 | 3.50 | 3.00 | 3.50 | 3.50 |
| Part B | Cyclomethicone | | 1.00 | 1.50 | | 1.00 | 1.50 |
| | Dimethicone | 12.00 | 12.00 | 12.00 | 12.00 | 12.00 | 12.00 |
| | Dimethicone (and) Dimethicone/Vinyl Dimethicone Crosspolymer | 5.00 | 5.00 | 5.00 | 5.00 | 5.00 | 5.00 |
| Part C | Titanium Dioxide (and) Aluminum Hydroxide (and) Dimethicone/-Methicone Copolymer (and) Hydrated Silica | 1.00 | 1.00 | 1.00 | 1.00 | 1.00 | 1.00 |

TABLE B1-continued water silicone formulations

| | INCI-Name/ Chemical-Name | % w/w (as supplied) | | | | | |
|---|---|---|---|---|---|---|---|
| | | Ex. B1 | Ex. B2 | Ex. B3 | Ex. B4 | Ex. B5 | Ex. B6 |
| Part D | Water | | | 1.50 | | | 1.50 |
| | Butylene Glycol | qs to 100 | qs to 100 | qs to 100 | qs to 100 | qs to 100 | qs to 100 |
| | Sodium Chloride | 3.00 | 3.00 | 3.00 | 3.00 | 3.00 | 3.00 |
| Part E | Alcohol | 1.00 | 1.00 | 1.00 | 1.00 | 1.00 | 1.00 |
| | | 5.00 | 5.00 | 5.00 | 5.00 | 5.00 | 5.00 |
| | Results: | | | | | | |
| | In-vitro SPF measurement | 15 | 19 | 30 | | | |
| | UVA Balance (according to DIN 67502) | 21 | 26 | 20 | | | |

The invention claimed is:

1. A process for the preparation of hydroxyphenylbenzophenone of formula

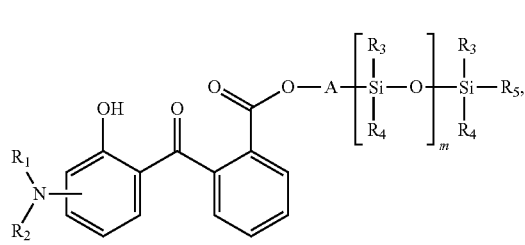
(1)

which comprises reacting a siloxanol compound of formula

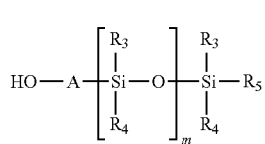
(1b)

with a benzophenone carboxylic acid or anhydride of the formula

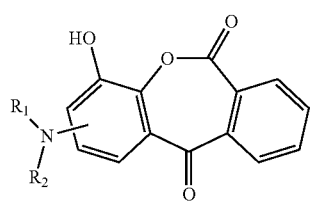
(1c)

wherein
$R_1$ and $R_2$ independently from each other are hydrogen; $C_1$-$C_{20}$alkyl; $C_2$-$C_{20}$alkenyl; $C_3$-$C_{20}$cycloalkyl; $C_3$-$C_{10}$cycloalkenyl; or $R_1$ and $R_2$ together with the linking nitrogen atom form a 5-6-membered heterocyclic ring;
$R_3$, $R_4$ and $R_5$ independently from each other are $C_1$-$C_4$alkyl; $C_1$-$C_4$alkoxy; or a radical of formula

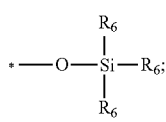
(1a)

$R_6$ is $C_1$-$C_6$alkyl;
A is a straight-chain or branched $C_3$-$C_6$alkylene, which is optionally interrupted by one or more *—O—*, or *—O—(CO)—* groups; and
m is 0; or a number from 1 to 5.

2. A process according to claim 1, wherein $R_1$ and $R_2$ are $C_1$-$C_{20}$alkyl.

3. A process according to claim 1, wherein $R_1$ and $R_2$ independently from each other are $C_1$-$C_5$alkyl.

4. A process according to claim 1, wherein $R_1$ and $R_2$ in formula (1) have the same definition.

5. A process according to claim 1, wherein A is $C_3$-$C_6$alkylen; or ($C_1$-$C_5$alkylene)-O—(CO)—($C_1$-$C_5$)alkylene.

6. A process according to claim 1, wherein m is 0.

7. A process according to claim 1, wherein $R_3$ and $R_4$ are a radical of formula

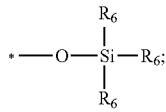
(1a)

wherein
$R_6$ is $C_1$-$C_6$alkyl.

8. A process according to claim 1, wherein $R_1$ and $R_2$ are $C_1$-$C_5$alkyl;
$R_3$ and $R_4$ are a radical of formula

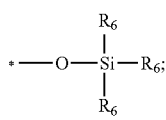
(1a)

$R_6$ is $C_1$-$C_5$alkyl;
A is $C_3$alkylene; and
m is 0.

* * * * *